United States Patent [19]

Friend et al.

[11] Patent Number: 5,656,294
[45] Date of Patent: Aug. 12, 1997

[54] COLONIC DELIVERY OF DRUGS

[75] Inventors: David R. Friend, Menlo Park; David Wong, San Francisco, both of Calif.

[73] Assignee: Cibus Pharmaceutical, Inc., Redwood City, Calif.

[21] Appl. No.: 486,974

[22] Filed: Jun. 7, 1995

[51] Int. Cl.$^6$ .............................. A61K 9/20; A61K 31/56; A61K 47/36

[52] U.S. Cl. .................... 424/465; 424/485; 424/488; 514/177; 514/178; 514/179; 514/180; 514/181; 514/182; 514/777; 514/780; 514/782

[58] Field of Search ...................... 514/2, 177, 178, 514/179, 180, 181, 182, 777, 780, 782; 424/461, 479, 481, 485, 488, 493, 496, 500, 465

[56] References Cited

U.S. PATENT DOCUMENTS

| | | | |
|---|---|---|---|
| 3,629,393 | 12/1971 | Nakamoto et al. | 424/470 |
| 4,389,393 | 6/1983 | Schor et al. | 424/480 |
| 4,994,276 | 2/1991 | Baichwal et al. | 424/488 |
| 4,999,200 | 3/1991 | Casillan | 424/480 |
| 5,096,714 | 3/1992 | Kuhrts | 424/488 |
| 5,108,758 | 4/1992 | Allwood et al. | 424/468 |
| 5,128,143 | 7/1992 | Baichwal et al. | 424/488 |
| 5,422,121 | 6/1995 | Lehmann et al. | 424/488 |
| 5,445,826 | 8/1995 | Kuhrts | 424/489 |
| 5,466,469 | 11/1995 | Kuhrts | 424/490 |

FOREIGN PATENT DOCUMENTS

| | | |
|---|---|---|
| 2053569 | 4/1992 | Canada . |
| 0 343 993 A1 | 11/1989 | European Pat. Off. . |
| 0 371 493 A1 | 6/1990 | European Pat. Off. . |
| 0 481 240 A2 | 4/1992 | European Pat. Off. . |
| 0 485 840 A2 | 5/1992 | European Pat. Off. . |
| 2 667 242 | 4/1992 | France . |
| 2 238 243 A | 5/1991 | United Kingdom . |
| WO 86/06627 | 11/1986 | WIPO . |
| WO 87/06241 | 10/1987 | WIPO . |
| WO 89/04673 | 6/1989 | WIPO . |
| WO 91/16881 | 11/1991 | WIPO . |
| WO 92/00732 | 1/1992 | WIPO . |

OTHER PUBLICATIONS

Adkin et al., "Colonic Transit of Different Sized Tablets in Healthy Subjects" *Journal of Controlled Release* (1993) 23:147–156.

Brondsted and Kopeck, "Hydrogels for Site–Specific Oral Drug Delivery: Synthesis and Characterization", *Biomaterials* (1991) 12:584–592.

Cummings, "Short Chain Fatty Acids in the Human Colon", *Gut* (1981), 22:763–779.

Damgé et al., "New Approach for Oral Administration of Insulin With Polyalkylcyanoacrylate Nanocapsules as Drug Carrier" *Diabetes* (1968) 37:246–251.

Davis et al., "Transit of Pharmaceutical Dosage Forms Through the Small Intestine" *Gut* (1986) 27:886–892.

Feely et al., "Investigating the Gastrointestinal Transit of Controlled Release Mini–Matrices Using Gamma Scintigraphy", *Proceed. Intern. Symp. Control. Rel. Bioact. Mater.* (1985) 12:94–95.

Hardy et al., (1987) "Evaluation of an Enteric–Coated Delayed–Release 5–Aminosalicyclic Acid Tablet in Patients With Inflammatory Bowel Disease" *Ailment. Pharmacol. Therap.* (1987), 1:273–280.

Holt, et al., "Effect of Gel Fibre on Gastric Emptying and Absorption of Glucose and Paracetamol", *Lancet* (1979) 1:636–639.

Jain et al., "Controlled–Release Tablet Formulation of Isoniazid", *Pharmazie* (1992) 47:277–278.

Khosla et al., (1989) "Gastrointestinal Transit of Non–Disintegrating Tablets in Fed Subjects" *International Journal of Pharmaceutics* (1989) 53:107–117.

Kopecek, "Polymers for Colon–Specific Drug Delivery", *Journal of Controlled Release* (1992) 19:121–130.

Latymer et al., "Measurement of Transit Time of Digesta Through Sections of Gastrointestinal Tract of Pigs Fed with Diets Containing Various Sources of Dietary Fibre (Non–Starch Polysaccharides)" *Arch. Anim. Nutr. Berlin* (1990) 40:667–680.

Marvola et al., "Gastrointestinal Transit and Concomitant Absorption of Verapamil from a Single–Unit Sustained–Release Tablet", *Drug Development and Industrial Pharmacy* (1987) 13(9–11):1593–1609.

Miranda et al., "High–Fiber Diets in the Treatment of Diabetes Mellitus" *Annals of Internal Medicine* (1978) 88:482–486.

Moore et al., "Absorption Enhancement of Growth Hormone from the Gastrointestinal Tract of Rats", *International Journal of Pharmaceutics* (1986) 34:35–43.

McIntire et al., "Different Fibers Have Different Regional Effects on Luminal Contents of Rat Colon", *Gastroenterology* (1991) 101:1274–1281.

Price et al., "Characterization of Colonic Transit of Nondisintegrating Tablets in Healthy Subjects", *Digestive Diseases and Sciences*, (1993) 38(6):1015–1021.

(List continued on next page.)

*Primary Examiner*—Jeffrey E. Russel
*Attorney, Agent, or Firm*—Cooley Godward LLP

[57] ABSTRACT

Pharmaceutical compositions for orally delivering a therapeutically effective amount of a drug to the colon without significant release of the drug in the upper GI tract after oral administration of the composition are described. The composition comprises about 0.5% by weight to about 10% by weight of the drug that is useful in treating a colonic disorder or that is absorbed from the colon; about 40% by weight to about 80% by weight of a hydrocolloid gum obtainable from higher plants; and about 10% by weight to about 50% by weight of a pharmaceutically acceptable binder. The compositions are useful for treating colon disorders in human subjects by administering a suitable amount to a subject in need thereof. A particularly preferred aspect is the process for preparing such composition in the form of a tablet.

14 Claims, No Drawings

OTHER PUBLICATIONS

Price et al., "The Effect of Meal Composition on the Gastrocolonic Response: Implications for Drug Delivery to the Colon" *Pharmaceutical Research* (1993) 10(5):722–726.

Rubinstein and Gliko–Kabir, "Synthesis and Swelling Dependent Enzymatic Degradation of Borax Modified Guar Gum for Colonic Delivery Purposes" *S.T.P. Pharma Sciences* (1995) 5:41–46.

Sakr and Elsabbagh, "Effect of Particle Size Distribution on the Disintegrating Efficiency of Guar Gum" *Pharm. Ind.* (1976) 38(8):732–734.

Salyers and Leedle, "Carbohydrate Metabolism in the Human Colon" *Human Intestinal Microflora in Health and Disease*, Chapter 6, pp. 129–146 (1983).

Spiller et al., "Emptying of the Terminal Ileum in Intact Humans: Influence of Meal Residue and Ileal Motility" *Gastroenterology* (1987) 92:724–729.

Trenev, "We Need Friendly Bacteria" *Total Health* (1988) 10:29–29.

Venter and Vorster, "Possible Metabolic Consequences of Fermentation in the Colon for Humans" *Medical Hypotheses* (1989) 29:161–166.

Waaler et al., "Biopharmaceutical Studies of Naftidrofuryl in Hydrocolloid Matrix Tablets" *International Journal of Pharmaceutics* (1992) 87:229–237.

Watanabe et al., "Factors Affecting Prednisolone Release from Hydrogels Prepared with Water–Soluble Dietary Fibers, Xanthan and Locust Bean Gums" *Chem. Pharm. Bull.* (1992) 40(2):459–462.

Woodley, "Peptidase Activity in the G.I. Tract: Distribution Between Luminal Contents and Mucosal Tissue", *Proceed. Intern. Symp. Control. Rel. Bioct. Mater* (1991) 18:337–338.

Yoshikawa et al., "Comparison of Disapearance from Blood and Lymphatic Delivery of Human Fibroblast Interferon in Rat by Different Administration Route", *J. Pharmacobio–Dyn.* (1985) 8:206–210.

COLONIC DELIVERY OF DRUGS

TECHNICAL FIELD

This invention relates to pharmaceutical compositions for oral administration to preferentially deliver drugs to the colon.

BACKGROUND

At the present time, there are no good orally-deliverable drug compositions that target treatment of various colon diseases such as chronic inflammatory diseases of the colon or diseases that require treatment by drugs that are absorbed through the colon. Also, there are no orally-deliverable drug compositions for peptides that release the peptides in a colonic environment where the peptides are not degraded to the same extent as peptides are degraded in the acid environment of the upper GI track, particularly the stomach.

Colon diseases include such conditions such as Crohn's disease, colitis (particularly ulcerative colitis), irritable bowel syndrome and the like. These diseases include a spectrum of inflammatory bowel disorders with overlapping clinical, epidemiologic and pathologic findings but without a definite etiology. Both Crohn's disease (CD) and ulcerative colitis (UC) are characterized by chronic inflammation at various sites of the GI tract, generally the colon (i.e., that part of the intestine from the cecum to the rectum). In treating these disease states, it is difficult to direct drugs that are specifically anti-inflammatory in nature and act topically to the desired site. For example, CD seems to affect the cecum primarily while UC seems to go past the second turn in the colon and affect the splenic flexure.

One of the families of compounds that are used in the treatment of this family of diseases are glucorcorticoids. These are thought to be useful in that the glucocorticoids have the capacity to prevent or suppress the development of the manifestations of this inflammation. The thought is that if the drugs can be administered to the inflamed area, the inflammation will recede and the body will ultimately be able to recover. Unfortunately, there are certain side effects the glucocorticoids exhibit if administered systemically and these side effects can be quite significant in treating any disease state. Another problem stemming from these side effects is that there is no way to deliver the drugs directly to the afflicted portion of the colon. Most of the oral formulations that are presently available disintegrate as they pass through the upper GI tract and thus, the steroids are absorbed into the body systemically and the subject being treated will experience some of the undesirable side effects.

The general approaches to delivering drugs to the colon include: 1) enteric coating designed to release drug in the more alkaline environment of the gastrointestinal tract, 2) bioerodible coatings and matrices, 3) prodrugs, 4) timed-release systems and, 5) sustained release systems that release drug after they transit through the small intestine and reach the large intestine.

It is known that certain hydrocolloids have a chemical structure that is subject to attack by the enzymes that are present in the colon, which enzymes will cause the structure of the hydrocolloids to degrade and breakdown. Thus, it has been thought that if a composition could be prepared that would be made of a drug useful for treating the colonic condition and that would pass through the upper GI tract without releasing the drug but would preferentially release it in the colon, the problem could be solved. Several attempts have been made to use a galactomannan-based composition (such as guar gum) to prepare compositions that are orally-administratable but which do not deliver a drug in the upper GI tract but instead make it through the tract to the colon. None of these have been successful. A paper by Rubinstein and Gilko-Kabir describes a borax-modified guar gum for colonic delivery purposes. However, that procedure requires that guar gum be chemically modified using borax in various concentrations to achieve the desired results. Other attempts have been made using glassy amylose to prepare compositions. These, too, were minimally successful.

It is also known that hydrocolloids that are obtainable from higher plants, such as guar gum, are used to increase the gastric residence time and the mean residence time in the gastrointestinal tract to deliver a drug which has the same bioavailability as the formulation of the drug which gives a systemic release profile. The concept is spelled out in co-pending application U.S. Ser. No. 08/348,515 filed Dec. 1, 1994. A broad range of hydrocolloid gum obtained from higher plants could be used to achieve those ends. The type of drug that could be used in the composition of that invention generally included nonpeptidic drug categories that exhibit a preferential window of absorption in the upper GI tract and/or that are generally susceptible to sustained release.

It has now been discovered that by carefully controlling the amount of a hydrocolloid that is obtainable from higher plants, such as guar gum, a composition can be prepared for compounds that are particularly useful for treating chronic inflammatory diseases of the colon (and other colon disorders such as irritable bowel syndrome, constipation, diarrhea, etc.) and for delivering compounds (e.g. peptides) to the colon for better absorption. The families of compounds for which this is particularly valuable includes the glucocorticoids, anticholenergics, 5-ASA, stimulant laxatives, peptides and certain antibodies.

OBJECTS OF THE INVENTION

An object of this invention is to provide a unit dosage composition comprising a drug useful for treating colonic disorders that is orally-administered and delivers the major amount of the drug preferentially to the colon of a human subject in need thereof.

Another object of this invention is to provide a unit dosage composition comprising a drug useful for treating colonic disorders or a drug that degrades in the upper GI track that is orally-administered and that goes through the upper GI track without releasing significant quantities of the drug to a human subject being treated.

Another object of this invention is to provide a unit dosage composition comprising a drug useful for treating colon disorders that is orally-administered and minimizes adverse systemic effects to a human subject being treated.

Another object of this invention is to provide a unit dosage composition comprising a drug useful for topically treating colon disorders that is orally-administered and delivers the major amount of the drug to the colon so the drug is released for topical treatment while minimizing systemic effects of such drug.

Another object of this invention is to provide a method for treating a human subject through oral administration of a unit dosage composition that achieves the foregoing objects of this invention.

Still another object of this invention is to provide a process for preparing a unit dosage tablet composition suitable for oral administration that attains the foregoing objects of this invention.

Other objects of this invention will be apparent to one of ordinary skill by reading the following specification and claims.

SUMMARY OF THE INVENTION

One aspect of this invention is a pharmaceutical composition for orally delivering a therapeutically effective amount of the drug to the colon without significant release of the drug in the upper GI track after all administration of the composition. The composition comprises about 0.5% by weight to about 10.0% by weight of the drug that is useful in treating the colonic disorder or that is absorbed from the colon; about 40% by weight to about 80% by weight of the hydrocolloid gum obtainable from higher plants; and about 10% by weight to about 50% by weight of the pharmaceutically acceptable excipient. Preferably the drug is a corticosteroid.

Another aspect of this invention is a method for treating colon disorders in a human subject, which method comprises orally administering to a human subject in need thereof a unit dosage composition as described above.

Still another aspect of this invention is a process for preparing a composition in a form of a tablet suitable for oral administration to a human subject. The tablet composition delivers a therapeutically effective amount of a drug that is useful to treat a colon disorder or that is absorbed from the colon without significant release in the upper GI track. The process comprises mixing about 0.5% by weight to about 10% by weight of such a drug; about 20% by weight to about 80% by weight of a hydrocolloid gum obtainable from higher plants; and about 10% by weight to about 50% by weight of the pharmaceutically acceptable excipient, then forming a tablet of the composition.

Other aspects of the invention will be apparent to one of ordinary skill of the art upon reading the following specification and the claims.

DESCRIPTION OF SPECIFIC EMBODIMENTS

The compositions of this invention are based on the observation that by carefully controlling the percentage of a hydrocolloid obtainable from a higher plant in an orally-administered dosage form and combining it with a suitable excipient and a particular family of drugs, a composition can be obtained which traverses the gastrointestinal tract without releasing any significant amount of drug, but when it reaches the colon, the drug is preferentially released due at least in part to the action of the enzymatic environment in the colon. The compositions and methods of this invention are particularly useful for colonic delivery of glucocorticoids, as well as other drugs (e.g. peptides) that might be inactivated if released in the upper gastrointestinal tract, to the colon without releasing any significant amount of the drug in the upper GI track as the composition travels through the entire GI tract. Generally, a relatively high percentage of the hydrocolloid gum obtainable from higher plants is present, namely at least 40% to about 80% (depending in part on the purity of the gum), with a lesser amount of a pharmaceutically acceptable excipient that provides binding and/or disintegrating capability for the composition as well as providing a minimal hardness for the tablet so that it can be prepared pharmaceutically. This amount is less than 50% but preferably more than 20% by weight of the composition. The remainder is a drug present at a level that is therapeutically effective and depends on the relative activity of the drug and its interaction with the composition. The drug may be useful for treating conditions of the colon (e.g., inflammatory diseases or other conditions requiring drugs that are absorbed from the colon).

The Compositions

One aspect of this invention is an orally-deliverable composition for preferentially delivering a therapeutically effective amount of a suitable drug to the colon without significant release of the drug in the upper GI tract upon oral administration of the composition to a subject in need thereof. A composition comprises about 0.1% weight to about 5.0% by weight of a suitable drug (e.g., for treating inflammatory colonic disorders); about 50% by weight to about 80% by weight of a hydrocolloid gum obtainable from higher plants; and about 20% by weight to about 50% by weight of a pharmaceutically acceptable excipient such as a binder. Other optional materials may be present that will assist in establishing the desired characteristics of the pharmaceutical composition.

The hydrocolloid that is used in the subject invention is a hydrocolloid that is obtainable from higher plants. By "higher plant" is meant an organism of the vegetable kingdom that lacks the power of locomotion, has cellulose cell walls, grows by synthesis of inorganic substances and includes the vascular plants (or tracheophytes) of the division Spermatophyta, particularly those of the class Angiospermae. The gums may be extracted from the roots, legumes, pods, berries, bark, etc. Thus, higher plants do not include algae, flagellates, bacteria, slime molds, fungi, mosses, ferns, horsetails and the like. Representative hydrocolloid gums obtainable from higher plants include guar gum, gum tragacanth, karaya gum (also referred to as kadaya gum) and locust bean gum. Others may be readily apparent to one of skill in the art. See, for example, "The Chemistry of Plant Gums and Mucilages" by Smith and Montgomery from ACS Monograph Series, No. 141, 1959, Reinhold Publishing Company and the 18th edition of the Merck Index. A particularly convenient and useful hydrocolloid is guar gum which is a neutral polysaccharide and consists of long galactomannan molecules with some side chain attachments. The hydrocolloids used in the subject invention have high viscosity exhibited upon hydration, are normally linear (at least about 90% by weight of the compound is the backbone chain), and will normally have high molecular weight, usually about $5 \times 10^5$ daltons, more usually greater than about $1 \times 10^6$ daltons. Generally, the hydrocolloid comes as a powdered hydrocolloid gum and exhibits a viscosity at a 1% concentration in a neutral aqueous solution of at least about 1,000 centipoise per second (cps) at 25° C. after 24 hours, using a Brookfield viscometer (model LDF) with a number 3 spindle at 90 rpms, preferably at least $2 \times 10^3$ cps and most preferable at least about $3 \times 10^3$ cps. See Meer Corporation, "An Introduction to Polyhydrocolloids." Guar gum is particularly useful in the composition of this invention and is prepared from the ground endosperms of *Cyamopsis tetragonolobus* which is cultivated primarily in India. Guar gum is available from commercial sources. For example, guar gum sold under the registered trademark "SUPERCOL" G3 having a particle size of about 75 to about 300 microns and SUPERCOL U having a particle size from about 20 to 100 microns are useful and are available from Aqualon Company in Wilmington, Del. Other sources of commercially available guar include Henkle, a Division of Emery Group, Cincinnati, Ohio or the Meer Corporation.

In general, the amount of the hydrocolloid that will be used is an amount that allows the composition to traverse the upper GI tract without significant disintegration and without releasing significant amounts of drug in the upper GI tract. Generally, that amount will be more than about 50% but less than about 80%. More preferably, the amount will be between 55% to about 65% by weight of the hydrocolloid gum. Generally more than about 50% of the drug will be released in the colon.

This invention provides a vehicle for delivering drugs preferentially to the colon. Among the drugs for which this will be useful are drugs for the treatment of chronic diseases of the bowel, including inflammatory diseases. These drugs may include certain glucocorticoids, stimulant laxatives, peptides, antibodies, ACE inhibitors, antichloinergics, and other drugs such as diphenoxylate, loperamide, codeine, metronidazole, 5-amino salicylic acid (5-ASA), sulfasalazine. Of these compounds, particularly valuable and therefore preferred are the glucocorticoids (also known as corticosteroids), particularly for treating irritable bowel diseases (IBD) and colitis. These include hydrocortisone (and pharmaceutically-acceptable salts or esters such as the acetate, cypionate, sodium phosphate, sodium succinate, butyrate, valerate, etc.), beclamethasone, beclamethasone dipropionate, betamethasone (and its pharmaceutically-acceptable salts or esters such as the benzoate, dipropionate, sodium phosphate, acetate, valerate, etc.) cortisone, cortisone acetate, dexamethasone, dexamethasone acetate, dexamethasone sodium phosphate, flunisolide, methylprednisone, methylprednisone acetate, methylprednisone sodium succinate, paramethasone acetate, prednisilone, prednisilone acetate, prednisilone sodium phosphate, prednisilone tebutate, prednisone, triamcinolone, triamcinolone acetinide, triamcinolone diacetate, triacsinilone hexacetonide, alclometasone dipropioante, amcinonide, clobetasol propionate, clocortilone pivalate, desonide, desoximetasone, diflorasone diacetate, fluocinolone acetonide, fluocinonide, fluorometholone, flurandrenolide, halcinonide, medrysone, mometasone furoate, budesonide, fluticasone, and the like. Other steroids may be apparent to one of ordinary skill in the art. The chemical names of these can be found at page 1451 of Goodman and Gillman's "The Pharmacological Basis of Therapeutics," 8th edition or in the Eleventh Edition of the Merck Index. Of these, dexamethasone, budesonide and fluticasone are preferred. Other drugs that are useful in this invention include stimulant laxatives (for example, docusate sodium, senna concentrates [sennosides], bisacodyl, potassium bitartrate, and the like), and peptides such as LHRH or its derivatives (e.g., leurprolide acetate, nafarelin, gosarelin, and the like). The amount of the active drug that will be included in the composition will vary depending upon the activity of the drug relative to the condition being treated. In general, there will be no more than about 20%, preferably less than 10% of the active compound in the composition with a minimum amount of about 0.1% by weight. Preferably, the amount will vary between about 1% to about 4% by weight.

In addition to the hydrocolloids available from higher plants and the active ingredients, there is included a component which acts as a disintegrant, binder and a hardness adjuster for the composition. In general, this excipient is needed to i.a., ensure that the composition of the invention will eventually be entirely disintegrated in the colon. Depending on the interactions between the active ingredient and the composition, the excipient may provide other characteristics that are useful. For example, it may help improve flowability, adhesion, disintegration, stability, hardness and other characteristics that are desirable. The excipients may include multiple substances having similar pharmaceutical function such as a binder or disintegrant or a similar structure such as a mixture of monosaccharides. Excipients that are known in the art to be useful include for example carbohydrates such as mono and disaccharides (i.e., lactose, sucrose, glucose, fructose, galactose); oligosaccharides such as dextrin; and hydrocolloid polysaccharides such as cellulose (particularly microcrystalline cellulose sold under the registered trademark "AVICEL"), semisynthetic cellulose ethers and derivatives thereof such as carboxymethyl cellulose, carboxypolymethelene cellulose, hydroxy propyl cellulose (HPC), hydroxy propyl methylcellulose (HPMC), and methyl cellulose. In some cases it may be useful to include compounds such as carboxypolymethylene, sold under the registered trademark "CARBOPOL" (e.g., CARBOPOL 934P) and cross-linked polymer of acrylic acid, sold under the registered trademark "CARBOMER".

The total amount of material in a tablet composition as a unit dosage form may vary between about 100 mg and about 1,000 mg but generally will be less than about 800 mg and preferably less than 500 mg for ease of swallowing. In general, the ratio of the hydrocolloid to the binder will be in the range of about 3 to 1 to about 1 to 1 on a weight basis.

EXAMPLES

Example 1

This example sets forth certain compositions of this invention in which the active ingredient is dexamethasone. The example provides guidance for showing whether a composition will meet certain objects of the invention.

A series of gum-based tablets designed to achieve differing profiles for the release of dexamethasone in the gastrointestinal tract were prepared. Formulations were selected on the basis of preliminary studies of the effects of excipients on tablet hardness and integrity in dissolution medium. Four dosage forms were chosen and tested in a three-part in vitro dissolution system. Three of these dosage forms represent compositions of this invention and target drug release preferentially to the colon. The fourth, fast-releasing dosage form was shown to release almost its entire drug load in the gastric fluid of the stomach for comparative purposes.

Tablet Ingredients

AVICEL PH200 (microcrystalline cellulose) was purchased from FMC Corporation. METHOCEL E50LV and E3 (HPMC) were obtained from Dow Corporation. USP grade, micronized dexamethasone was purchased from Upjohn Company. EMCOMPRESS (dicalcium phosphate) as purchased from Mendell. Magnesium stearate was obtained from Whittaker, Clark & Daniels. Coarse grade (G3) and free grade (U) guar gum were purchased from Aqualon.

Powder mixing and tablet preparation

For the small initial batches (i.e., 20 g), powders were generally mixed simply by spatulation before tableting. When larger batches were required (i.e., 150 g), powder ingredients (except magnesium stearate) were first sieved (mesh #40) and mixed with spatulation method, then with a V-blender for 10 minutes. Magnesium stearate, as a lubricant for tableting, was added and the final powder mixture was blended for another 10 minutes.

All powders (except dexamethasone) for the dosage forms used in this Example 1 were passed through 40 mesh size sieve. Dexamethasone was then pre-mixed with approximately one-sixth of total guar gum powder by spatulation to obtain uniformity of drug content.

The tablets were manually compressed with a rotary tableting machine [Model dual pressure press, F. J. Strokes Machine Company, Philadelphia, Pa., with punches (Cups: concave, shallow, monoradius, diameter of $^{13}/_{32}$")]. The tablets weighed ~300–350 mg each and contained approximately 9–13 mg drug to give a final concentration of 3% by weight. The formulations of the four selected formulations are:

A. 60.5% G3-grade guar, 36% HPMC E3, 3% Dex, 0.5% Mg Stearate

B. 60.5% G3-grade guar, 36% HPMC E50LV, 3% Dex, 0.5% Mg Stearate

C. 24.5% G3-grade guar, 72% AVICEL, 3% Dex, 0.5% Mg Stearate

D. 60.5% U-grade guar, 36% EMCOMPRESS, 3% Dex, 0.5% Mg Stearate

Formulations A, B and D are representative of the invention.

Measurement of physical characteristics

1. Tablet Hardness

The hardness test for tablets was performed by Vanderkamp VK 200 Tablet Hardness Tester (VanKel Industries, Inc., Edison, N.H.). A tablet was placed at the strain gauge. As the moving jaw pressed the tablet against it, the force was recorded at the movement the initial fracture was detected.

2. Material Lost

Tablets were weighed before (a) and after (b) dissolution. Then, they were dried at 60° C. They were weighed again (c). To determine the amount of material lost, the following calculations were performed:

1. The weight of tablets was measured before (a) and after (b) the dissolution.
2. The tablets were dried and weighed (c).
3. The amount of material lost=a–c; the amount of water absorbed % w/w=(b–a)/c*100%.

3. Friability

The friability test for tablets was performed by Tablet Friabilater (VanKel Industries, Inc., Edison, N.H.). Approximately 4 g ($w_o$) of dedusted tablets were subjected to 100 free falls of 6 inches in a rotating drum at 25 rpm and were then reweighed (w). The friability, f, was found by using the formula:

$$f=100*(1-w_o/w)$$

Values of f from 0.8 to 1.0% were regarded as the upper limit of acceptability.

Dissolution testing

1. Preparation of simulated gastric fluid (SGF)

Sodium chloride (7 g) and pepsin (11.2 g) were co-dissolved in 24.5 ml of hydrochloric acid. Deionized water was added to make the final volume equal to 3500 ml.

2. Preparation of simulated intestinal fluid (SIF)

Monobasic potassium phosphate (23.8 g) was dissolved in 875 ml of water. Sodium hydroxide (665 ml, 0.2N) and 1400 ml of water were then added. Pancreatin (35 g) was added and the resulting solution was adjusted with 0.2N sodium hydroxide to a pH of 7.5±0.5. The solution was subsequently diluted with water to a final volume of 3500 ml.

3. Preparation of simulated colonic fluid (SCF)

SCF was comprised of homogenized stool samples from healthy volunteers or from colitis patients (specimens homogenized if not sufficiently fluid). Preparations were used undiluted.

4. Dissolution testing

Tablets were weighed and placed in 500 ml of simulated gastric fluid (SGF) for 2 hours with stir speed set at 50 rpm (USP method 2; paddle). Samples (5 ml) were taken at specified intervals for analysis of drug content and replaced with fresh medium. For testing drug release in SIF, tablets were subsequently transferred using an aluminum dish into vessels containing 500 ml of SIF (USP method 2; paddle). During transfer, the fluid was removed carefully by tilting the dish. Tablets were immersed in SIF for a period of 4 hours and stirred at a speed of 50 rpm. During this period, 5 ml samples were collected at specific time points and replaced with fresh medium. For further dissolution testing in colonic fluids, the tablets were then transferred into 10 g of SCF. The medium was mixed by dipping a plunger up and down 8 to 9 times per minute inside the test tube. Samples (0.5 g) were taken at specific intervals over an 18 hour period without replacement of the colonic medium. The temperature was maintained at 37° C. throughout the experiment.

Quantitative analysis

Quantitation was done by averaged single point internal standard calibration. A standard solution containing 50 µg/ml dexamethasone (Dex) and 50 µg/ml triamcinolone acetonide (TrAce) was prepared. The standard mixture was injected before and after every 20 sample injections. The respective standard and internal standard peak areas were then averaged for use as the single point calibration factor. Calibration curves were previously generated for both Dex and TrAce. The respective curves were determined to be linear and went through zero. The standards were thus considered suitable for single point calibration.

All of the sample amounts were carefully measured (by mass or volume) and then spiked with 30 µl of a 1 mg/ml Dex/TrAce mixture. The spike is equal to 30 µg each of Dex and TrAce. After the samples were prepared (according to the descriptions in following sections) they were injected onto the HPLC column. The resulting concentrations of Dex and TrAce were calculated from the respective standards as such:

$$C_{smp}=C_{std}(A_{smp} \div A_{std}) \qquad (1)$$

Where:

$C_{smp}$=concentration of the sample $C_{std}$=concentration of the standard $A_{smp}$=area of the sample $A_{std}$=area of the standard The original concentration of Dex in the sample was then calculated as follows:

$$X=[(M*t/T)-d]/Z \qquad (2)$$

Where:

X=concentration of Dex

M=measured concentration of Dex from equ 1

T=measured concentration of TrAce from equ 2 t=mass (in µg) of TrAce spiked into the sample d=mass (in µg) of Dex spiked into the sample Z=sample amount (mg or ml)

Samples were analyzed by HPLC for quantitation of dexamethasone released. The results were expressed as percent drug released relative to the amount in the intact tablet.

Analytical sample preparation

1. Gastric fluid samples

For analysis of samples from SGF, 0.5 ml of sample was placed in a test tube to which was added 30 µl of a mixture of 1 mg/ml Dex/Triamcinolone (TrAce) mixture (internal standard for calibration). Two ml of 100% ethanol were added followed by 150 µl of 0.2N NaOH solution to bring the pH to 5.0. The sample was mixed by repeated inversion before injecting onto the HPLC column for analysis of drug content.

2. Intestinal fluid samples

For analysis of samples from SIF, 0.5 ml of sample was transferred to a test tube to which was added 30 μl of a 1 mg/ml Dex/TrAce mixture. Two ml of 100% ethanol were then added and the sample mixed by repeated inversion before injection onto the HPLC column for analysis of drug content.

3. Colonic fluid samples

For analysis of samples from SCF, 150–500 mg of sample was added to a test tube and the mass was recorded. Thirty μl of a standard mixture of Dex and TrAce (1 mg/ml) was then added along with 2 ml water and 2 ml 100% ethanol. The mixture was then sonicated for 5 minutes and the coarse solids were removed by centrifugation. Resulting supernatants were transferred to a syringe and filtered through a 0.45 micron filter. The samples were mixed by repeated inversion prior to injection onto the HPLC column for analysis.

Hardness and friability testing was performed on the four dosage forms examined in drug release studies (prepared by premixing the Dex). The results are shown below in Table 1.

TABLE 1

| Formulation | Hardness (kp) (n = 7) | Friability (%) (n = 1) |
|---|---|---|
| C. | 14 ± 1 | 0.04 |
| D. | 2.2 ± 0.8 | 0.89 |
| A. | 4.5 ± 0.6 | 0.28 |
| B. | 3.6 ± 0.6 | 0.19 |

Drug Release

The results from three-part dissolution testing systems show the profile for drug release varied as a function of formulation. A tablet made from formulation C demonstrated "fast" release of the drug with approximately 90% of the Dex originally contained in the tablet being released into SGF by the 2 hour time point. This tablet significantly disintegrated in the presence of SGF. In contrast, the tablet prepared from formulations A, B and D showed very little release of drug until placed in SCF with the drug release profiles for tablets prepared from formulation A showing substantial drug release in SCF. Though a measurable amount of drug was detected in SCF, the majority of drug release from A, B and D tablets preferentially occurred in the presence of SCF. Complete disintegration of these tablets was observed in the SCF whereas very little disintegration was observed when immersed in SIF over the same time period.

On the basis of results obtained, formulations A, B and D are capable of releasing little if any drug in the stomach and small intestine while preferentially releasing drug in a sustained manner once the tablets reach the colon. Though total disintegration of the tablets was observed by 24 h, total release of Dex was not detected in these experiments. The stirring conditions in the SCF system were relatively mild; a likely explanation for these results, therefore, is that all the Dex was released from these dosage forms but not uniformly distributed throughout the viscous dissolution medium. The fast-releasing tablets release drug primarily in the stomach and/or small intestine. This dosage form C provides a relatively rapid input of drug into the body as compared to the three other dosage forms. In addition to rapid drug release, C was observed to disintegrate completely in SGF within 1–2 hours.

Example 2

This example provides a pharmacoscintigraphic evaluation of the four formulations of Example 1 and shows the preferential release of the active ingredient, dexamethasone, into the colon from the three formulations of this invention. A study was designed to investigate the gastrointestinal transit and disintegration of the four formulations of Example 1 and to evaluate the subsequent absorption of dexamethasone released from the preparations. The study was a double blind, parallel group design in which blocks of eight healthy subjects received one of the four different formulations. Thirty-two healthy volunteers (18 male, 14 female) were administered tablets weighing approximately 333 mg each and containing approximately 2.7% dexamethasone (i.e. not more than 9 mg dexamethasone per tablet) made in accordance with Example 1. Each subject received a single tablet radiolabelled with $^{153}$Sm.

Clinical Supplies

Neutron activation methods were used to radiolabel dosage forms. These techniques require the addition of a stable isotope within a formulation; subsequent irradiation in a neutron source converts the isotope into a gamma emitting radionuclide. By using these neutron activation methods, exposure of workers to radiation can be minimized and complicated delivery systems can be labelled easily and efficiently. In order to validate this technique, the irradiation process must be shown to have no effect on the formulation, i.e. the preparation must behave in a similar manner both prior to and following the irradiation procedure. Dosage forms were irradiated for six minutes in a neutron flux of $10^{12}$ n cm$^2$s$^1$ 48 hours prior to dosing and in vitro testing demonstrated that neither the addition of the samarium oxide nor the neutron activation process affected the performance of the dosage forms or the stability of the drug.

Dosing Details

The volunteers arrived fasted (from midnight) at the study site. Anterior and lateral anatomical markers containing 0.1 MBq $^{99}$Tc$^m$ were taped to the skin over the right lobe of the liver. A single radiolabelled dosage form was administered to each of the volunteers at approximately 8:00 am with a 240 ml of water.

Anterior scintigraphic images were recorded at frequent intervals for up to 16 hours, using a gamma camera (General Electric Maxicamera) with a 40 cm field of view and fitted with a low energy parallel hole collimator. Images were recorded at approximately 10 minute intervals up to 12 hours post-dose and then at approximately 30 minute intervals until 16 hours post-dose. Return visits were made to the clinical unit at 24 and 36 hours post-dose to allow the acquisition of further images. Images were of 50 seconds duration for the first 9 hours after dosing but the acquisition time was then extended to 80 seconds until 16 hours post-dose. Images obtained at 24 and 36 hours post-does were acquired for 120 seconds. The volunteer remained moderately active during the study period and all images were acquired with the subjects standing in front of the gamma camera. The images were recorded using a Bartec computer system and were stored on optical disk for subsequent analysis.

A standard light lunch, dinner and supper were provided at 4, 9 and 14 hours post-dose, respectively. Each subject drank 200 ml of water at two hours post-dose and fluids were allowed ad libitum after lunch. At the end of the study day 1, subjects were instructed to fast until returning to the clinical unit the following morning. Food was only allowed ad libitum after the 24 hour image and blood sample.

Blood Sampling

Venous blood samples (10 ml) were withdrawn via an intravenous cannual or by venepuncture according to the following time schedule:

0 (pre-dose), 1.0, 2.0, 4.0, 6.0, 8.0, 10.0, 12.0, 14.0, 16.0 24.0 and 36.0 hours post-dose.

The first 2 ml of blood withdrawn via the cannual was discarded and the subsequent 10 ml was withdrawn into serum separation monovettes. The cannulae were frequently flushed through with saline during the course of study day 1. The total amount of blood taken from each volunteer for the study, including pre- and post-study medical, was 190 ml.

The samples were left at room temperature for approximately 30 minute until a clot was formed. The samples were then centrifuged at approximately 3000 rmp (or 1800 g) for 7 minutes at 4° C. The resulting serum fraction was split into two aliquots by pipeting into two pre-labelled polypropylene screw cap tubes. Samples were flash frozen and then stored immediately at 20° C. A sample was subsequently shipped on dry ice to an assay center assay.

Scintigraphic Data Analysis

The data from the study were analyzed in line with pharmaceutical Profiles' Standard Operating Procedure for Quality Control of Gamma Camera Data Analysis to obtain the following parameters:

I. Gastric emptying time;

II. Small intestinal transit time; (a) Time of complete tablet disintegration and (b) anatomical location.

III. Colon Arrival time; (a) Time of initial tablet disintegration and (b) anatomical location.

IV. Transit histograms.

The recorded time of movement of the tablet from the stomach to the small intestine was taken as the mid-term between the times recorded for the two images about the transition. The times for colon arrival and initial and complete tablet disintegration were determined in the same manner. Small intestinal transit time was calculated by subtracting the gastric emptying time from the time at which initial colon arrival occurred. Initial tablet disintegration was defined as the time taken to detect signs of release of radioactive marker from the tablet in consecutive images while complete release was defined as the time at which all the radiolabel had dispersed within the gastrointestinal tract and no signs o a distinct 'core' remained.

Gastrointestinal transit

The average gastric emptying time (I), average small intestinal transit time (II), and average colon arrival time (III), all given in minutes, are summarized in Table 2. As can be seen all of formulations A, B and D stayed intact long enough to reach the colon.

TABLE 2

Gastrointestinal Transit Summary Formulation

| Formulation | I | II | III |
|---|---|---|---|
| A | 56 ± 42 | 258 ± 96 | 313 ± 89 |
| B | 33 ± 23 | 218 ± 33 | 251 ± 21 |
| C | (1) | (1) | (1) |
| D | 52 ± 43 | 243 ± 85 | 295 ± 73 |

(1) rapid disintegration prevented determination

Tablet Disintegration

The average initial tablet disintegration time in minutes (IV(a)) and anatomical location (IV(b)) and the average time for complete tablet disintegration in minutes (V(a)) and anatomical location (V(b)) are summarized in Table 3.

TABLE 3

Tablet Disintegration Summary

| Formulation | IV(a) | IV(b) | V(a) | V(B) |
|---|---|---|---|---|
| A | 104 ± 60 | U I | 472 ± 161 | C |
| B | 345 ± 138 | C | 741 ± 194 | C |
| C | 10 ± 17 | S | 125 ± 310 | S |
| D | 213 ± 97 | I | 734 ± 228 | C | s = stomach; c = colon; I = intestine; UI = upper intestine

Following administration of Formulations A, B, C and D initial tablet disintegration occurred on avenge at 104±60 minutes (range 40 to 227 minutes) post-dose, 345±138 minutes (range 174 to 630 minutes) post-dose, 10±17 (range 1 to 48 minutes) post-dose and 213±97 minutes (range 138 to 442 minutes) post-dose. Initial disintegration occurred in the stomach for each subject receiving Regimen C and also in the upper intestines for volunteers receiving Regimen A. In seven of the eight subjects that received Regimen D the tablets began to disintegrate in the small intestine whilst in subject 005, disintegration was only observed to commence after the tablet had reached the ascending colon. In six of the eight subjects who received Regimen B initial disintegration of the tablets was also observed following colon arrival. However, it was noted that a small amount of radioactive material 'leached' from each of the four formulations shortly after administration of the preparations. Initially this material was observed to disperse throughout the gastrointestinal tract, however, it could often not be detected in subsequent images. This material is thought to result from progressive erosion of the surface of the tablets due to the continual peristaltic action of the gut. For this reason, initial disintegration was recorded as the midpoint between the two images after which dispersed radioactive marker was observed in consecutive images.

Complete tablet disintegration was defined as the time at which all the radiolabel had dispersed within the gastrointestinal tract and no signs of a distinct 'core' remained. Complete tablet disintegration occurred on average at 472±161 minutes (range 305 to 769 minutes; n=8) post-dose, 741±194 minutes (399 to 934 minutes; n=8) post-dose, 125±310 minutes (range 1 to 829 minutes; n=7) post-dose and 734±228 minutes (range 354 to 892 minutes; n=5) post-dose for Regimens A, B, C and D respectively. Complete tablet disintegration was observed in the colon for each subject receiving Regimens A, B and D. Complete disintegration did not occur in the first 16 hours post-dose in three of the eight subjects who received Regimen D and, in the remaining five subjects who received this formulation, disintegration occurred distally. Complete disintegration was observed more proximally in the colon in those subjects receiving Regimens A and B with disintegration of Formulation B typically occurring more distal to that of Formulation A. Distribution of the radiolabel within the colon at 24 and 36 post-dose was typical for all four formulations and in line with previous scintigraphic studies.

Complete disintegration occurred in the stomach in six of the eight subjects receiving Regimen C. However, in subject 032 complete disintegration occurred in the ascending colon and disintegration must have occurred in the large bowel in subject 017 since radioactive marker was still apparent in the colon 24 hours after dosing. The reason for the dichotomy in the results for these two subjects receiving Regimen C is unclear, but may be that the rate of hydration of hydrophilic polymers is critical to the formation of a gel layer, which in turn determines the integrity properties of the actual tablet.

It is possible that in 6 of the 8 subjects, the gel layer did not form quickly resulting in rapid tablet disintegration while in subjects 017 and 032 hydration of the polymer occurred rapidly, thereby significantly improving tablet integrity.

The scintigraphic data suggests that each of the four formulations behaved in a unique manner making it possible to distinguish between them. Formulation C showed early rapid release in the majority of cases. In three of the eight subjects who received Regimen D, complete disintegration of the tablets did not occur during the initial sixteen hour imaging period. In these cases complete release of the material occurred overnight and by virtue of the anatomical location of the marker at 24 hours post-dose, it could be concluded that release occurred somewhere in the large bowel. Release from Regimen A occurred more proximally in the large bowel while release from Regimen B occurred in the distal colon in five of the eight subjects who received this formulation.

Thus, formulations A, B and D (representative of compositions of this invention) all show preferential disintegration in the colon.

Example 3

By following the procedures of Example 1 but substituting the following compounds, similar compositions are prepared:

A. Budesonide
B. Fluticasone
C. Predisolone
D. Predisone
E. Hydrocortisone

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A pharmaceutical composition for orally delivering a therapeutically effective amount of a drug to the colon without significant release of the drug in the upper GI tract after oral administration of the composition, which composition comprises about 0.5% by weight to about 10.0% by weight of a corticosteroid drug useful in treating a colonic disorder;

about 40% by weight to about 80% by weight of a hydrocolloid gum obtainable from higher plants; and about 20% by weight to about 50% by weight of a pharmaceutically acceptable excipient.

2. The composition of claim 1, wherein the corticosteroid is present in an amount of about 1% by weight to about 4% by weight.

3. The composition of claim 1, wherein the corticosteroid is dexamethasone, budesonide, fluticasone, prednisone, prednisolone or hydrocortisone.

4. The composition of claim 1, wherein the hydrocolloid is guar gum, locust bean gum, gum tragacanth or karaya gum.

5. The composition of claim 1, wherein the hydrocolloid is guar gum.

6. The composition of claim 1, wherein the composition comprises about 1% by weight to about 4% by weight of the corticosteroid drug;

about 55% by weight to about 65% by weight of a hydrocolloid gum obtainable from higher plants;

about 30% by weight to about 45% by weight of a pharmaceutically acceptable binder.

7. A method for treating colon disorders in a human subject, which method comprises orally-administering to a human subject in need thereof a unit dosage composition that comprises about 0.5% by weight to about 10% by weight of a corticosteroid drug useful in treating colonic disorders;

about 40% by weight to about 80% by weight of a hydrocolloid gum obtainable from higher plants;

about 10% by weight to about 50% by weight of a pharmaceutically acceptable disintegrant.

8. The method of claim 7 wherein the composition comprises about 0.5% by weight to about 5.0% by weight of the corticosteroid drug;

about 50% by weight to about 70% by weight of a hydrocolloid gum obtainable from higher plants;

about 25% by weight to about 50% by weight of a pharmaceutically acceptable disintegrant.

9. The method of claim 8, wherein the corticosteroid is present in an amount of about 1% by weight to about 4% by weight.

10. The method of claim 9, wherein the corticosteroid is dexamethasone, budesonide, fluticasone, prednisone, prednisolone or hydrocortisone.

11. The method of claim 7, wherein the hydrocolloid is guar gum, locust bean gum, gum tragacanth or karaya gum.

12. The method of claim 11, wherein the hydrocolloid is guar gum.

13. The method of claim 8, wherein the composition comprises about 1% by weight to about 4% by weight of the corticosteroid drug;

about 55% by weight to about 65% by weight of a guar gum; and about 30% by weight to about 45% by weight of a pharmaceutically acceptable disintegrant.

14. A process for preparing a composition in the form of a tablet suitable for oral administration to a human subject, wherein the tablet composition delivers a therapeutically effective amount of a drug useful to treat colon disorders into the colon without significant release of the drug in the upper GI tract, which process comprises (a) mixing about 0.5% by weight to about 10.0% by weight of a corticosteroid drug useful in treating colonic disorders;

about 40% by weight to about 80% by weight of a hydrocolloid gum obtainable from higher plants;

about 10% by weight to about 50% by weight of a pharmaceutically acceptable excipient; and (b) forming a tablet.

* * * * *